(12) United States Patent
Shi

(10) Patent No.: US 11,318,461 B2
(45) Date of Patent: May 3, 2022

(54) FLUID COLLECTION UNIT AND RELATED DEVICES AND METHODS

(71) Applicant: NowDiagnostics, Inc., Springdale, AR (US)

(72) Inventor: Qinwei Shi, Richmond Hill (CA)

(73) Assignee: NOWDIAGNOSTICS, INC., Springdale, AR (US)

( * ) Notice: Subject to any disclaimer, the term of this patent is extended or adjusted under 35 U.S.C. 154(b) by 645 days.

(21) Appl. No.: 15/915,791

(22) Filed: Mar. 8, 2018

(65) Prior Publication Data

US 2018/0272338 A1 Sep. 27, 2018

Related U.S. Application Data

(60) Provisional application No. 62/584,314, filed on Nov. 10, 2017, provisional application No. 62/469,343, filed on Mar. 9, 2017.

(51) Int. Cl.
*B01L 3/00* (2006.01)
*A61B 10/00* (2006.01)

(52) U.S. Cl.
CPC ........ *B01L 3/5027* (2013.01); *A61B 10/0051* (2013.01); *A61B 2010/0006* (2013.01); *A61B 2010/0009* (2013.01); *B01L 2200/0621* (2013.01); *B01L 2400/0406* (2013.01)

(58) Field of Classification Search
CPC .......... A61B 10/0051; A61B 5/150213; B01L 3/5027; B01L 2200/0621; B01L 2400/0406
See application file for complete search history.

(56) References Cited

U.S. PATENT DOCUMENTS

| 5,739,041 | A | 4/1998 | Nazareth et al. |
| 6,248,598 | B1 | 6/2001 | Bogema |
| 6,303,081 | B1 * | 10/2001 | Mink ................. A61B 10/0051 422/412 |
| 7,238,538 | B2 | 7/2007 | Freitag et al. |
| 7,785,865 | B2 | 8/2010 | Qinwei |
| 8,119,393 | B2 | 2/2012 | Qinwei |
| 8,865,454 | B2 * | 10/2014 | Jonsmann ............. B01L 3/5027 435/283.1 |
| 9,678,069 | B2 * | 6/2017 | Gunnerson ...... A61B 5/150213 |
| 2004/0019301 | A1 | 1/2004 | Wong et al. |

(Continued)

FOREIGN PATENT DOCUMENTS

| CN | 102147419 A | 8/2011 |
| JP | H11505608 A | 5/1999 |

(Continued)

OTHER PUBLICATIONS

PCT International Search Report and Written Opinion for application PCT/IB2018/051532 dated Jun. 1, 2018.

(Continued)

*Primary Examiner* — Daniel L Cerioni
*Assistant Examiner* — Raymond P Dulman
(74) *Attorney, Agent, or Firm* — Alston & Bird LLP

(57) ABSTRACT

Described herein is a fluid collection unit comprising: a receptacle for passively collecting a fluid sample; and a fluid flow path in fluid communication with the receptacle, the fluid flow path passing through the unit for directing the fluid sample from the receptacle to an opposing end of the unit.

23 Claims, 15 Drawing Sheets

(56) References Cited

U.S. PATENT DOCUMENTS

| | | |
|---|---|---|
| 2005/0096563 A1 | 5/2005 | Liang |
| 2005/0106749 A1* | 5/2005 | Braig ................. G01N 21/0303 |
| | | 436/169 |
| 2006/0074347 A1 | 4/2006 | Eguchi et al. |
| 2008/0081341 A1 | 4/2008 | Maher et al. |
| 2010/0050789 A1 | 3/2010 | Stroup |
| 2010/0122587 A1* | 5/2010 | Sun .................... A61B 10/0051 |
| | | 73/864 |
| 2014/0272941 A1 | 9/2014 | Gunnerson et al. |
| 2014/0316302 A1 | 10/2014 | Nonnemacher et al. |
| 2016/0011188 A1 | 1/2016 | Anderberg et al. |
| 2018/0169656 A1* | 6/2018 | Trietsch ................. C12M 23/16 |

FOREIGN PATENT DOCUMENTS

| | | |
|---|---|---|
| JP | 2000199761 A | 7/2000 |
| JP | 2002181812 A | 6/2002 |
| JP | 2003532076 A | 10/2003 |
| JP | 2014182136 A | 9/2014 |
| WO | WO 01/81915 A1 | 11/2001 |
| WO | WO 2004/038382 A1 | 5/2004 |
| WO | WO-2009/143601 | 12/2009 |
| WO | WO-2013/155617 | 10/2013 |

OTHER PUBLICATIONS

JP Office Action for Japanese application 2019-571118 dated Jan. 28, 2022.

\* cited by examiner

FLUID COLLECTION UNIT AND RELATED DEVICES AND METHODS

CROSS-REFERENCE TO RELATED APPLICATIONS

This application claims the benefit of U.S. Provisional Application Ser. No. 62/584,314, filed Nov. 10, 2017, and U.S. Provisional Application Ser. No. 62/469,343, filed Mar. 9, 2017, each of which is herein incorporated by reference in its entirety for all purposes.

FIELD

The present invention relates to collection of fluid samples. More specifically, the present invention is, in aspects, concerned with fluid collection units and related methods and devices comprising same.

BACKGROUND

Saliva test devices are known and conventionally require a subject to expectorate saliva into a small tube, which is both difficult and uncomfortable. In addition, this typically results in a sample containing many bubbles. Other conventional devices involve a sponge or pad, which is used to collect saliva in the mouth. These require a large volume of saliva and still generally require that the saliva be squeezed from the sponge or pad prior to use.

For example, U.S. Pat. No. 6,248,598 describes a device representative of devices that require an absorbent material. The device described in this patent is a saliva sampling device including an expresser cup, an absorbent foam swab capable of absorbing a fluid specimen, and a flexible tether affixed to the foam swab. The foam swab is used to collect a sample of a fluid specimen such as saliva, and the tether is adapted to enable a user to sanitarily draw the saturated foam swab into the expresser cup in which the foam swab becomes compressed: and the absorbed fluid is expressed therefrom in a drop by drop fashion. The device also may include a platform having a reagent strip for absorbing the expressed fluid to reveal test results. The device may also include a divider for separating the expressed fluid into two or more aliquots prior to the testing thereof such that one of the aliquots may be used for confirmation or later testing of the fluid. In one embodiment, the expresser cup includes a conical cross section to effect gradual compression of the foam swab.

U.S. Patent Application Publication No. 2005/0096563 describes a device for collecting an expectorated oral fluid specimen for testing comprising a collection chamber having a specimen reservoir space and a headspace, and a vent, and a hollow tube capable of conducting oral fluid from the oral fluid donor's mouth to the specimen reservoir space of the collection chamber. The headspace is for storing oral fluid foams and the vent is for air to escape the chamber when the oral fluid is being collected into the collection chamber. The tube and the collection chamber are either permanently connected or separate with the device having a connection mechanism allowing the connection of the two. The device may further comprise an assay reagent component for detecting an analyte of the oral fluid specimen. The device provides simple means for oral fluid collection and testing, and especially useful in point-of-collection testing of oral fluid specimens.

There is a need for alternative compositions to overcome or mitigate at least some of the deficiencies of the prior art, or to provide a useful alternative.

BRIEF SUMMARY

In accordance with an aspect, there is provided a fluid collection unit comprising:
a receptacle for passively collecting a fluid sample; and
a fluid flow path in fluid communication with the receptacle, the fluid flow path passing through the unit for directing the fluid sample from the receptacle to an opposing end of the unit.

In an aspect, the receptacle comprises an indentation in the fluid collection unit.

In an aspect, the indentation is substantially cylindrical.

In an aspect, the indentation comprises an open sidewall in fluid communication with the fluid flow path.

In an aspect, the collection unit further comprises a region of concavity for directing fluid towards the receptacle.

In an aspect, the region of concavity is formed in a wall of the unit.

In an aspect, the region of concavity is substantially parallel with and above the fluid flow path.

In an aspect, the region of concavity comprises an open bottom wall in fluid communication with the fluid flow path.

In an aspect, the open bottom wall is sized to allow sufficient surface pressure such that, in use, fluid will not enter the fluid flow path through the open bottom until a front of fluid reaches the open bottom while passing through the fluid flow path.

In an aspect, the open bottom wall is sized so that large air bubbles or solid materials can be blocked from entering the fluid flow path.

In an aspect, the fluid flow path comprises a proximal constriction.

In an aspect, the fluid flow path holds from about 10 µl to about 200 µl of fluid.

In an aspect, the fluid flow path holds from about 25 µl to about 50 µl of fluid.

In an aspect, the fluid flow path holds about 40 µl of fluid.

In an aspect, the fluid flow path is in communication with a lateral flow membrane.

In an aspect, the fluid flow path is formed by mating a top half of the unit with a bottom half of the unit.

In an aspect, the unit allows for collection and flow of the fluid from the proximal end to the distal end of the unit and into a lateral flow membrane in fluid communication with the unit in a single step.

In an aspect, the fluid is oral fluid.

In an aspect, the collection unit further comprises a cover.

In an aspect, the cover is fully removable.

In an aspect, the cover is hinged such that it remains attached to the unit when the unit is in use.

In an aspect, the collection unit does not comprise an absorbent pad or sponge for collecting the fluid.

In an aspect, the collection unit does not require the addition of a buffer or diluent to effect flow of the fluid through the fluid flow path.

In accordance with an aspect, there is provided a lateral flow device comprising the fluid collection unit described herein.

In an aspect, the fluid collection unit is detachable from the lateral flow device.

In an aspect, the device comprises a window through which a test result can be viewed.

In an aspect, the device is transparent.

In an aspect, the device comprises a handle.

In an aspect, the handle is an indented circle for supporting a thumb or finger.

In an aspect, the handle is detachable from the device.

In an aspect, the device comprises a lateral flow membrane.

In accordance with an aspect, there is provided a one-step method of collecting a sample, the method comprising inserting the collection unit described herein in or near a sample and allowing the sample to be drawn into the fluid flow path.

In an aspect, the sample is saliva and the method comprises inserting the collection unit into the mouth, such as under the tongue or in the cheek pocket.

In an aspect, the obtained sample is substantially bubble-free.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION

Figure 1:
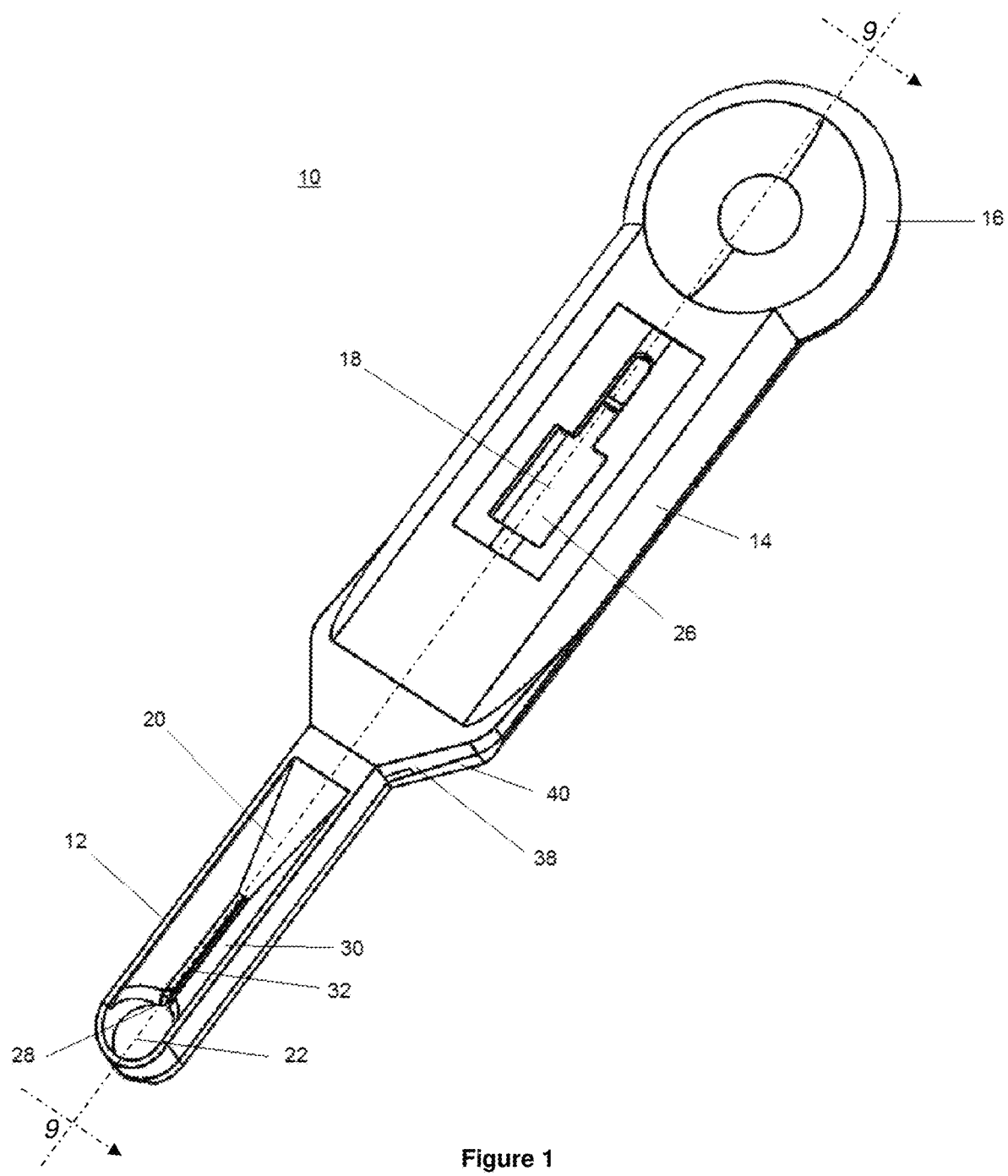
FIG. 1 shows a perspective view of a first embodiment of a lateral flow device described herein.
Figure 2:
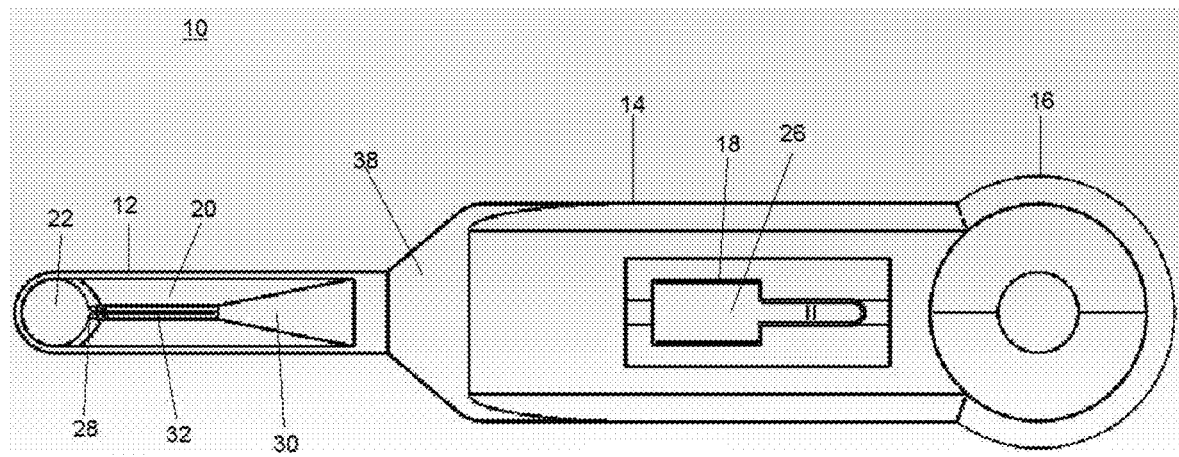
FIG. 2 shows a top plan view of the lateral flow device of FIG. 1.
Figure 3:
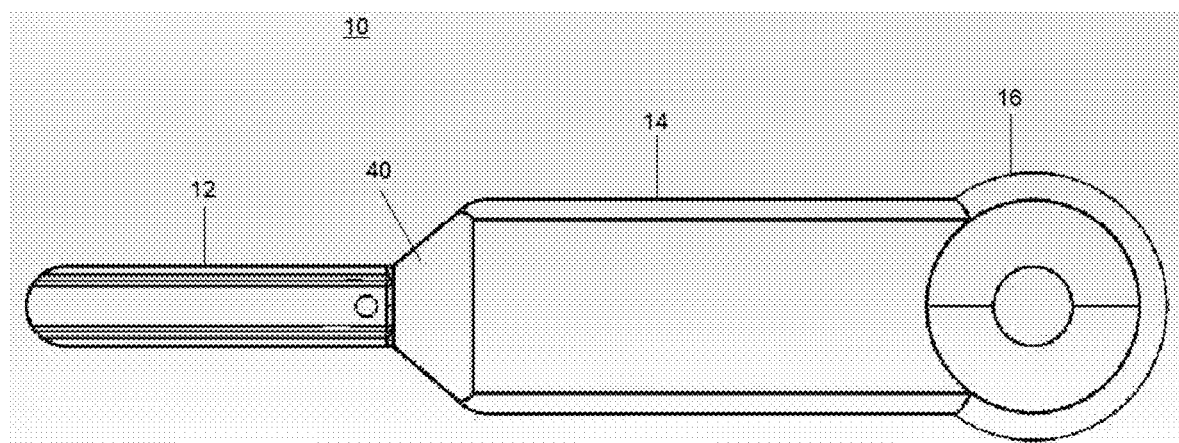
FIG. 3 shows a bottom plan view of the lateral flow device of FIG. 1.
Figure 4:
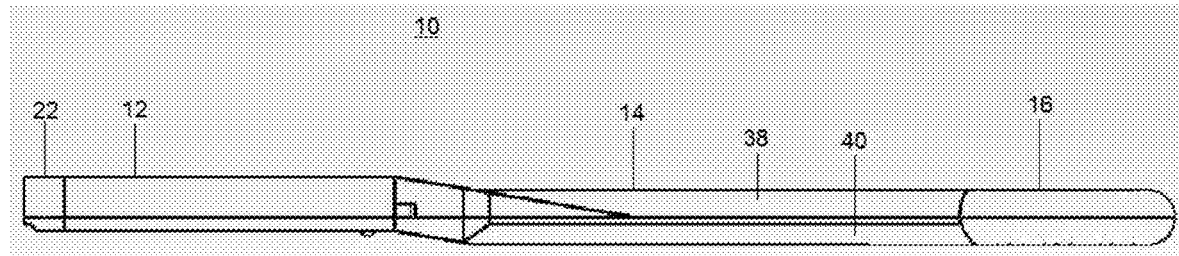
FIG. 4 shows a side view of the lateral flow device of FIG. 1.
Figure 5:
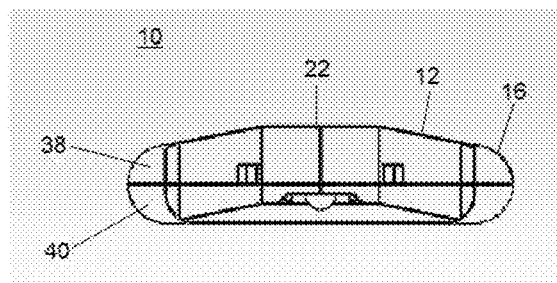
FIG. 5 shows a front view of the lateral flow device of FIG. 1.
Figure 6:
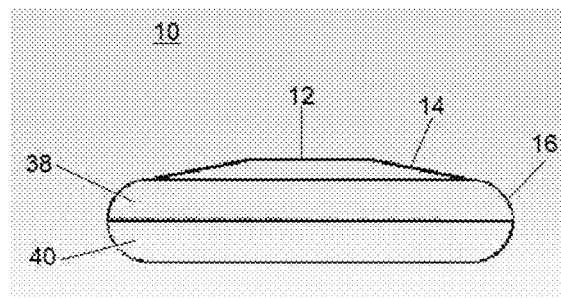
FIG. 6 shows a back view of the lateral flow device of FIG. 1.

Described herein, in aspects, are fluid collection units for obtaining a fluid sample. The fluid collection units may advantageously be included as part of a lateral flow device. While the fluid collection units described herein are particularly advantageous for collecting saliva samples, they may find use in collecting any type of fluid sample. In certain aspects, the fluid collection units passively collect the sample, for example, saliva, so that no expectoration of the saliva is required. The device may simply be placed in the mouth at a location so that the user can comfortably push saliva to the fluid collection opening at the top. In certain aspects, the fluid collection unit may be placed under the tongue or in a cheek pocket. Through a combination of capillary action and gravity forces, a sufficient yet small volume of saliva will be collected in the unit.

In this way, the collection units described herein may avoid collection of bubbles and/or large particulates in the saliva, which can affect accurate volume control and fluid flow leading to failure of a subsequent assay, and may also avoid the multiple steps required when saliva is collected with a sponge or pad, subsequently requiring squeezing out the saliva from the sponge or pad. Due to its higher fluid recovery and associated reduced fluid wasting, the fluid collection units described herein allow for easier fluid collection.

In aspects, the collection units and lateral flow devices described herein can achieve a one-step operation, wherein the device is placed in the mouth, saliva is collected, and a test result is obtained without requiring extra steps of expelling a sample from a sponge or pad, or applying a buffer solution, waiting for more sample to be collected, or waiting for bubbles to settle out of a fluid sample.

Definitions

The term "proximal" as used herein refers to portions of the collection unit or device that are closer to the end comprising the receptacle, whereas the term "distal" as used herein refers to portions of the collection unit or device that are closer to the end comprising the handle. The terms "upstream" and "downstream" refer to flow of a fluid from the proximal end (upstream) to the distal end (downstream).

The term "analyte" is intended to encompass any chemical or biological substance that is measured quantitatively or qualitatively. In typical aspects, the analyte is one that would be found in a saliva sample. Analytes can include small molecules, proteins, antibodies, DNA, RNA, nucleic acids, carbohydrates, lipids, organic anabolites or metabolites, virus components or intact viruses, bacteria components or intact bacteria, cellular components or intact cells and complexes and derivatives thereof. The human salivary glands secrete a rich mixture of biological chemicals, electrolytes, proteins, genetic material, polysaccharides, and other molecules. The level of each salivary component varies considerably depending on the health status of the individual and the presence of disease (oral or systemic) or the presence of drugs. By measuring these components in the saliva, it is possible to screen for a variety of things, including, but not limited to, infections, allergies, hormonal disturbances, neoplasms, drug use, and to obtain genetic material for subsequent testing.

For example, the collection units described herein find particular use in point of care devices to identify overdoses or roadside testing devices to identify drivers under the influence of alcohol or *cannabis*. Drugs that can be tested using collection units described herein include, but are not limited to, psychedelic agents, psychostimulants, sedatives, depressants, abused inhalants, hypnotics and alcohol. According to a particular embodiment, the one or more analytes to be detected are one or more drugs selected from the group of alcohol, opiates, cocaine, cannabinoids such as tetrahydrocannabinol (THC), amphetamines, methamphetamines, morphine, benzodiazepines, 1-(1'-phenylcyclohexyl) piperidine (PCP), barbiturates, methadone, and heroin or other opioids with a morphine-like action, such as, but not limited to, codeine, papaverine, noscapine, hydrocodone, or fentanyl. Derivatives or metabolites of these drugs may also be detected.

The analyte to be tested may be a drug of abuse, some of which are listed above, or it may be a drug that is often mistakenly overdosed on, such as acetaminophen. Further, the analyte may be a disease marker, such as troponin or C-reactive protein. Numerous examples of such markers exist and would be well known to a skilled person.

In other aspects, the analyte to be tested may be a genetic sample, such as those used by 23andMe™ or other DNA testing companies. Such companies typically require that a saliva sample be collected by an end user and returned to the company for testing. The saliva collection tubes used by these companies are typically the type that you must expectorate into, which can be a less than comfortable experience for the user.

The term "passive" or "passively" in reference to collecting a saliva sample is intended to exclude active efforts by the end user to expectorate or spit into the collection unit. Rather, passive collection means that the collection unit is placed into the mouth, typically under the tongue or in a cheek pocket, and saliva secretions are collected simply by virtue of the collection unit being placed in proximity to the secretions. Some mouth movement would be expected during use, and such movement is encompassed by the term "passive," provided it is not the act of actively spitting into the collection unit.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect of the invention.

It will be understood that any component defined herein as being included may be explicitly excluded from the claimed invention by way of proviso or negative limitation, whether implicitly or explicitly defined herein. For example, in an aspect, the devices herein do not use a sponge or collection pad for absorbing saliva as an initial step in the testing method.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Lateral Flow Device

FIGS. 1 to 9 show a first lateral flow device 10. As shown, the device 10 comprises a fluid collection unit 12 and a body 14. The body 14 contains a handle 16 and a window 18, through which results of an assay can be read visually or by a machine. The device 10 is typically transparent, but can be of any desired color and opacity and combinations thereof, provided the test can still be read. It will be understood that in a completely transparent device 10, the window 18 is optional.

Figure 8:
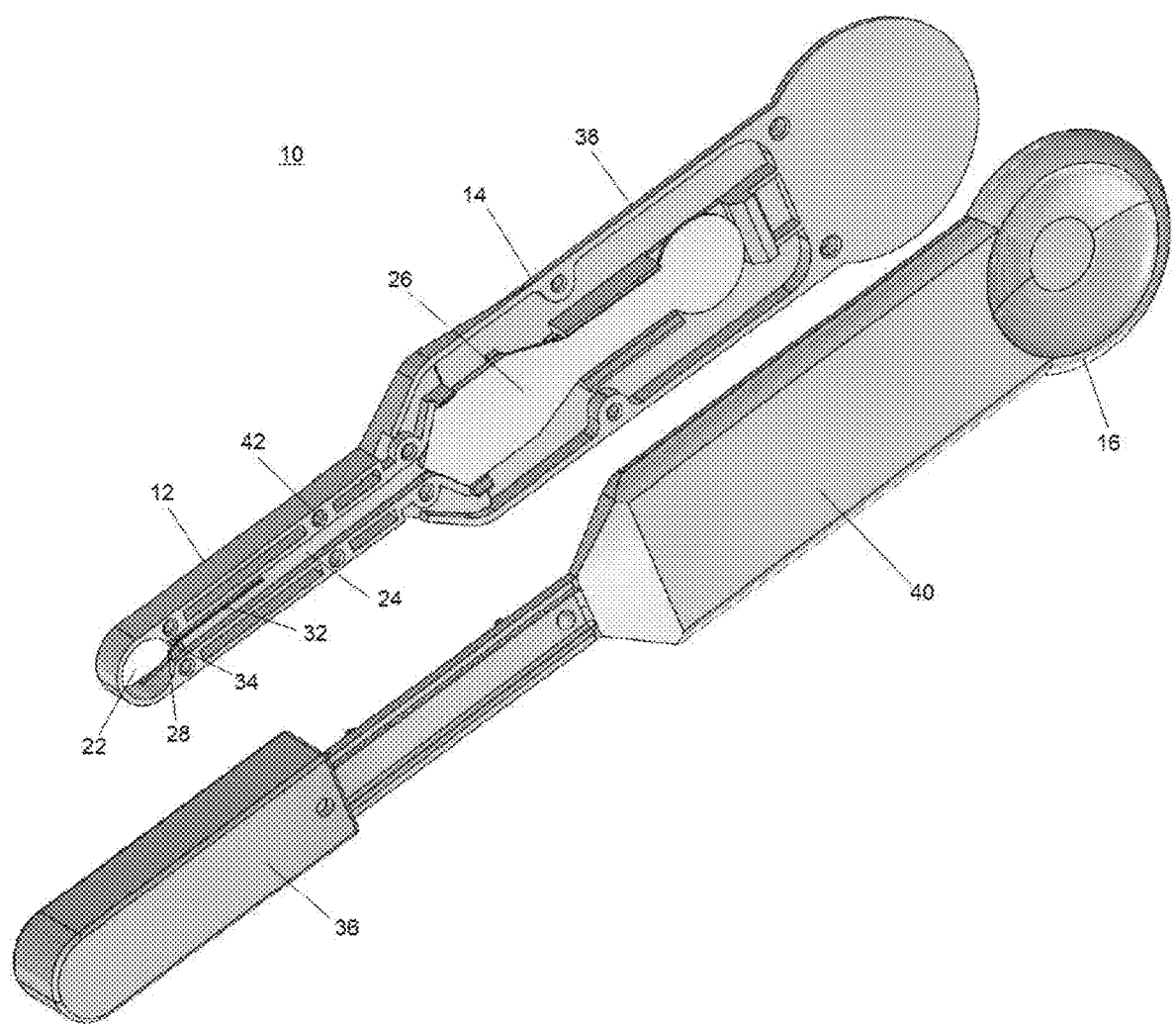
FIG. 8 shows a bottom exploded perspective view of the lateral flow device of FIG. 1 with addition of a lateral flow membrane and a device cover.

The fluid collection unit 12 typically comprises an elongate body comprising a region of concavity 20 and a receptacle 22. The region of concavity 20 and the receptacle 22 both lead to a fluid flow path 24, which is best seen in FIG. 8. The fluid flow path 24 functions to direct a fluid sample from the receptacle 22 to a lateral flow membrane 26 at opposite ends of the collection unit 12.

In certain aspects, the volume held by the fluid flow path 24 is rationally selected so as to be equal to or greater than the volume required for accurate function of the lateral flow membrane 26. In this way, the test will not initiate until a sufficient amount of sample is present in the collection unit 12, as the fluid front must reach the lateral flow membrane 26 for the test to begin. In aspects, the fluid flow path 24 has a volume of from about 10 µl to about 200 µl, such as from about 10 µl to about 100 µl, such as about 25 µl to about 50 µl, such as about 40 µl.

The receptacle 22 is typically a cylindrical indentation integrally formed in the collection unit 12. The receptacle 22 has an open sidewall 28 through which fluid in the receptacle 22 can enter the fluid flow path 24. The region of concavity 20 assists in directing additional fluid towards the receptacle 22.

As shown, the region of concavity 20 is formed in a wall above the fluid flow path 24 and comprises three slanted walls 30 that converge together at an open bottom wall 32 that is contiguous with the fluid flow path 24. As shown, two of the slanted sidewalls 30 cooperate to form in part the receptacle 22.

The open bottom wall 32 of the region of concavity 20 is sized to allow surface pressure to stop fluid flow such that, in use, fluid will not enter the fluid flow path 24 through the open bottom wall 32 until a front of fluid from the receptacle 22 reaches the open bottom wall 32 while passing through the fluid flow path 24. This assists in both drawing in fluid from the region of concavity 20 while reducing the likelihood of bubbles entering the fluid flow path 24 or otherwise interrupting the fluid in the fluid flow path 24 with air.

Figure 9:
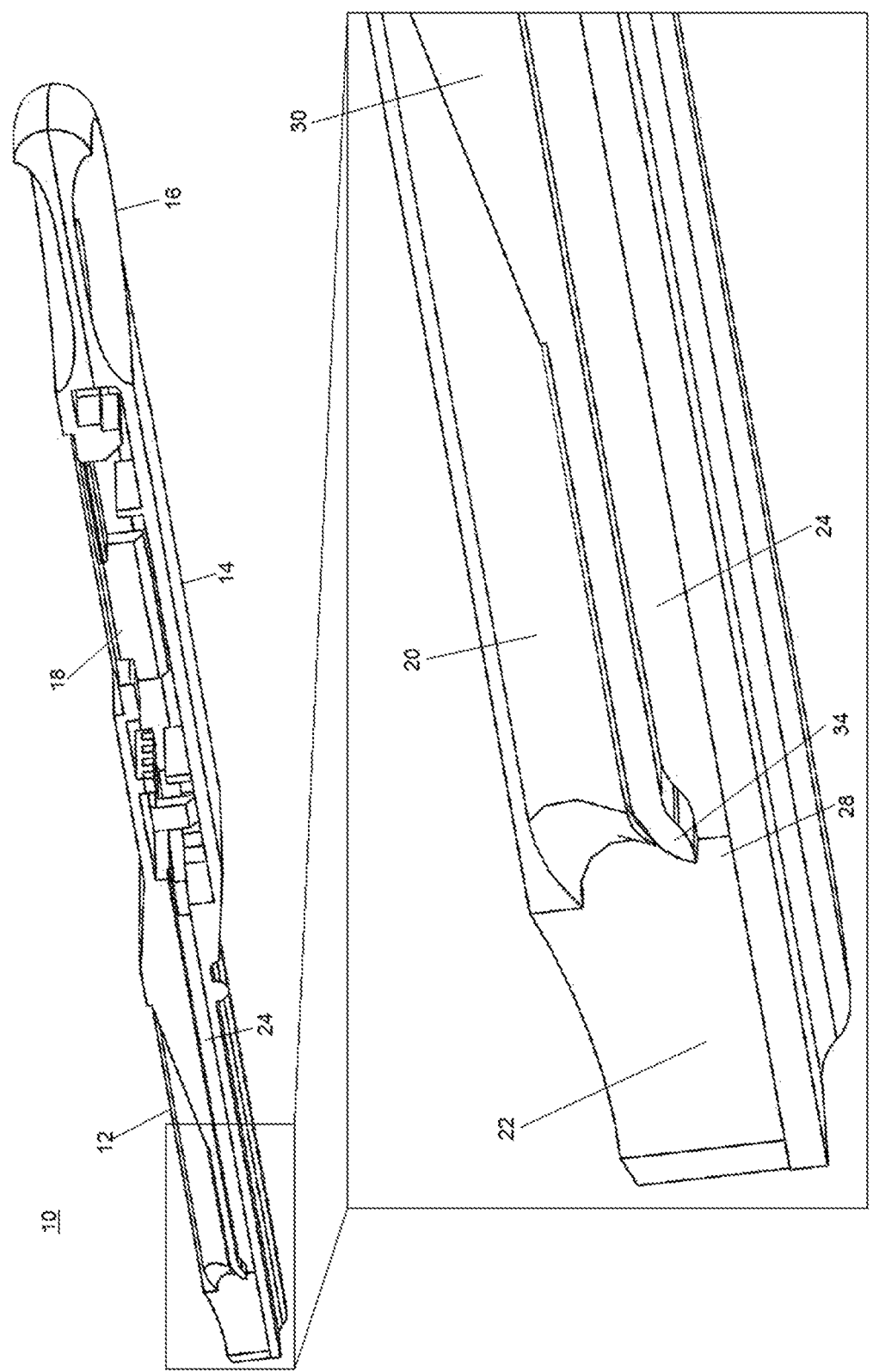
FIG. 9 shows a cross-sectional view along line 9-9 of the lateral flow device of FIG. 1.

As shown in FIGS. 8 and 9, the fluid flow path 24 comprises a constriction 34 near the receptacle 22. The constriction 34 is simply a narrowing of the fluid flow path 24, thereby locally reducing its cross-sectional area. In doing so, the constriction 34 increases the capillary force of the fluid surface at the leading edge of the fluid sample in the fluid flow path 24 relative to the remaining surface of the fluid sample. If too little fluid is present in the receptacle 22 upstream of the constriction 34, the fluid in the fluid flow path 24 will not flow to ensure test will not start without enough sample present. However, once sufficient fluid has pooled in the receptacle 22, the destruction of the fluid surface at the constriction 34 will allow flow to continue along the fluid flow path 24. The size of constriction 34 is selected to reduce the likelihood of a bubble entering the fluid flow path 24.

The collection unit 12 may be integral with the device 10 or it may be separable from the rest of the device 10. In certain aspects, the collection unit 12 is frangibly coupled in the device 10 so that the collection unit 12 can be easily snapped off after use for disposal and/or for inserting at least a portion of the device 10 into a reader for measuring the test result, as such readers may not be sized to fit the collection unit 12 when attached to the body 14.

Figure 7:
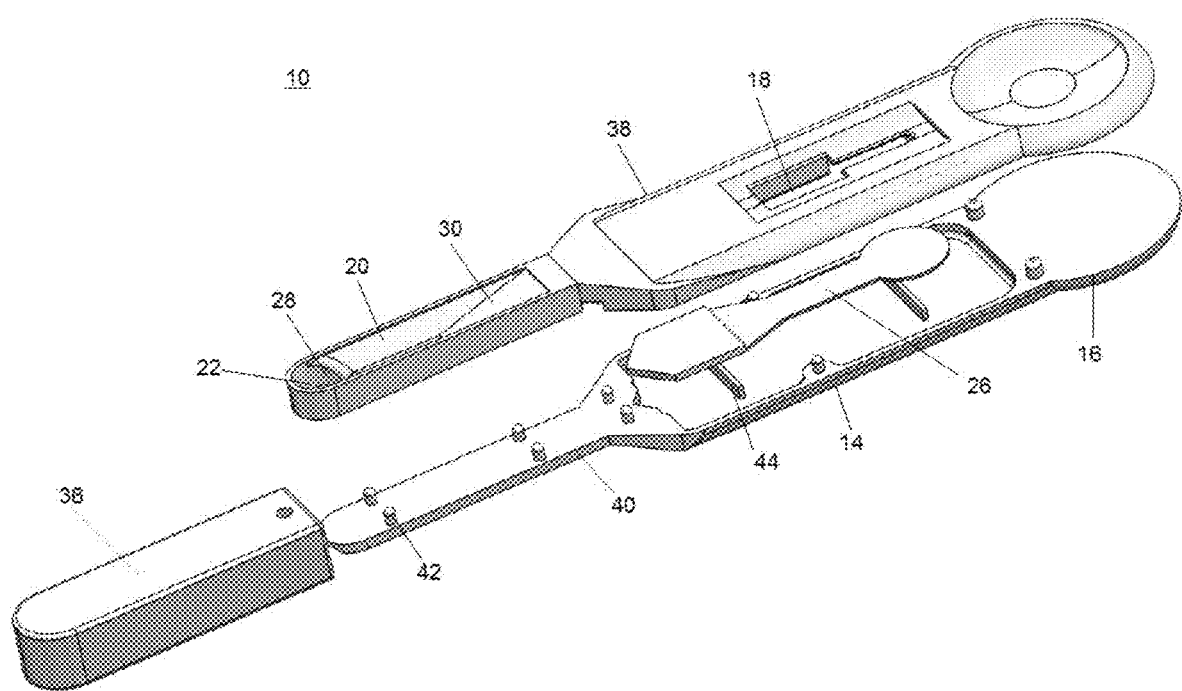
FIG. 7 shows a top exploded perspective view of the lateral flow device of FIG. 1 with addition of a lateral flow membrane and a device cover.

The collection unit 12 is typically provided with a cover 36 as shown in FIGS. 7 and 8. The cover 36 is removable so that the collection unit 12 can be used. The cover 36 can then be placed back on the collection unit 12 for sanitary and/or protective reasons. The cover 36 may be completely removable or it may, in aspects, remain partially attached to the device 10 and/or the collection unit 12 to reduce the chances of the cover 36 being misplaced or otherwise contaminated.

The device 10 typically comprises a handle 16, which, like the collection unit 12 may be frangibly coupled in the device 10 so that the handle 16 can be snapped away from the rest of device 10 and a conventional reader can be used with the rest of device 10. The handle 16 is typically rounded with an indent sized to facilitate handling with a thumb or finger.

The device 10 is typically formed by mated upper 38 and lower 40 portions, as shown in FIGS. 7 and 8, for ease of manufacturing and insertion of a desired lateral flow membrane 26. The device 10 could also be formed as a single unit. As shown, there are mated friction-fit components 42 that hold the upper 38 and lower 40 portions together. The upper 38 and lower 40 portions also contain guides 44 that securely hold the lateral flow membrane 26 in position so that it is in fluid communication with the fluid flow path 24.

As can be seen in FIGS. 7 and 8, the receptacle 22, region of concavity 20, and fluid flow path 24 are all formed in the upper portion 38 of the device 10. It will be understood that one or more of these features could be formed in part or in whole by the bottom portion 40 of the device 10.

FIGS. 10 to 16 show a second lateral flow device 110, which is constructed somewhat differently from the first lateral flow device 10, but operates under similar principles. As shown, the device 110 comprises a fluid collection unit 112 and a body 114. The body 114 contains a handle 116 and a window 118, through which results of an assay can be read visually or by a machine. The device 110 is typically transparent, but can be of any desired color and opacity and combinations thereof, provided the test can still be read. It will be understood that in a completely transparent device 110, the window 118 is optional.

Figure 10:
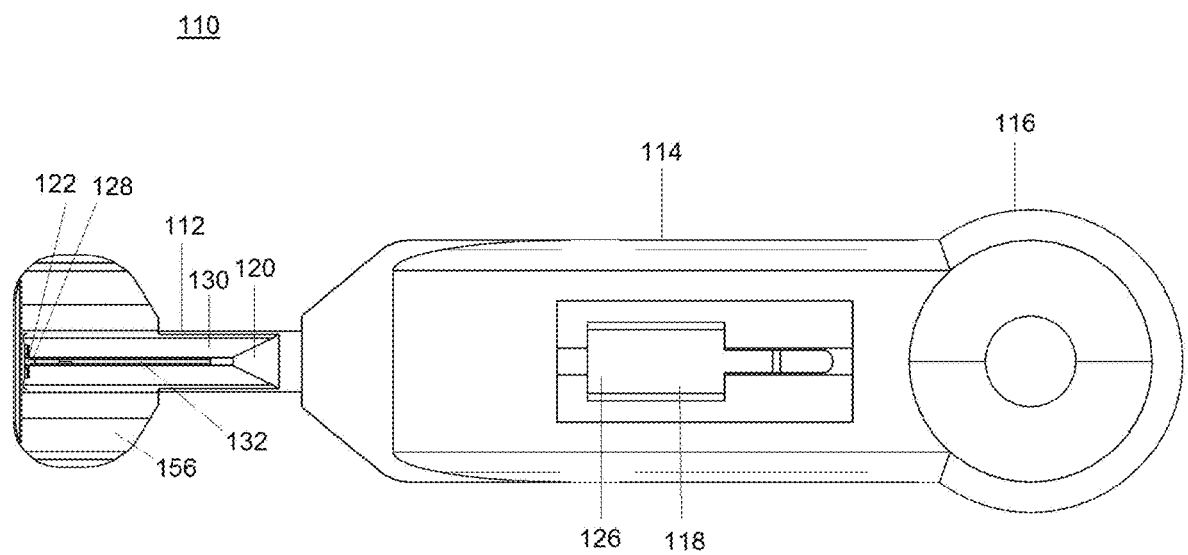
FIG. 10 shows a top plan view of a second embodiment of a lateral flow device described herein.
Figure 16:
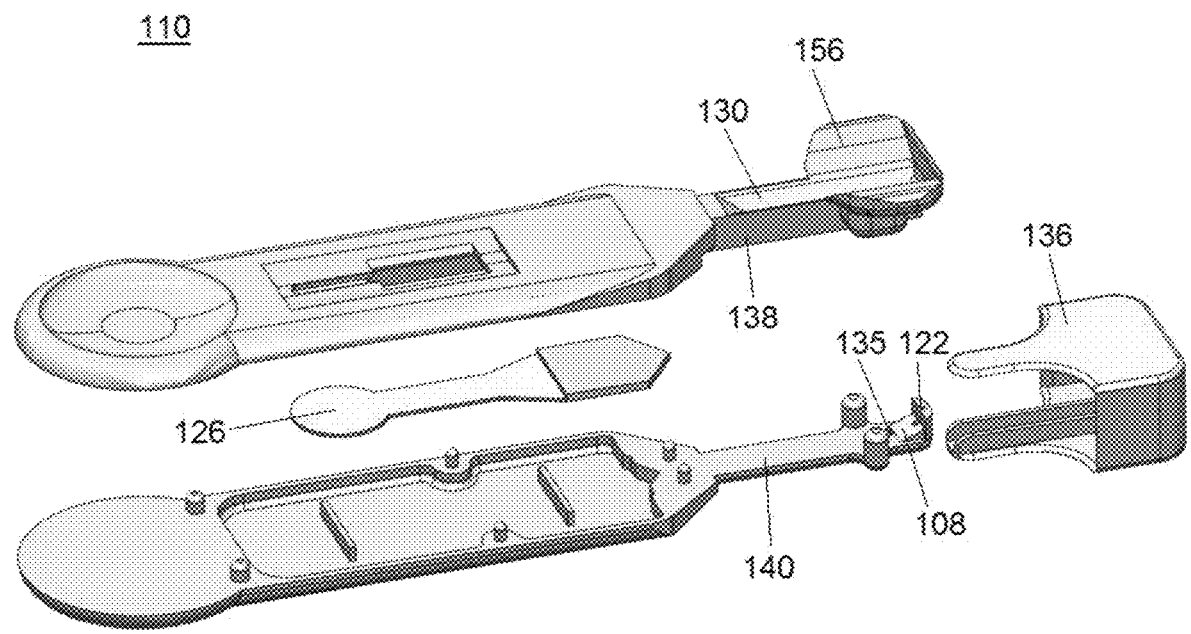
FIG. 16 shows a top exploded perspective view of the lateral flow device of FIG. 10 in the presence of a lateral flow membrane and a device cover.

The fluid collection unit 112 typically comprises an elongate body comprising a region of concavity 120 and a receptacle 122. In this aspect, the receptacle 122 is much smaller than the receptacle 22 described above in relation to FIGS. 1-9. Receptacle 122 is simply a small channel or opening leading to a fluid flow path 124. This design effectively reduces dead volume in the fluid collection unit 112. The region of concavity 120 also leads to the fluid flow path 124, as described above. The fluid flow path 124 functions to direct a fluid sample from the receptacle 122 to a lateral flow membrane 126 at opposite ends of the collection unit 112. As shown in FIGS. 10 and 16, the receptacle 122 is surrounded by flanges 156 that assist in collecting and directing the fluid sample towards the receptacle 122.

In certain aspects, the volume held by the fluid flow path 124 is rationally selected so as to be equal to or greater than the volume required for accurate function of the lateral flow membrane 126. In this way, the test will not initiate until a sufficient amount of sample is present in the collection unit 112, as the fluid front must reach the lateral flow membrane 126 for the test to begin. In aspects, the fluid flow path 124 has a volume of from about 10 µl to about 200 µl, such as from about 10 µl to about 100 µl, such as from about 25 µl to about 50 µl, such as about 40 µl.

The receptacle 122 is typically a small vertical channel integrally formed in the collection unit 112. The receptacle 122 has an open sidewall 128 through which fluid in the receptacle 122 can enter the fluid flow path 124. The region of concavity 120 assists in directing additional fluid towards the receptacle 122.

As shown, the region of concavity 120 is formed in a wall above the fluid flow path 124 and comprises three slanted walls 130 that converge together at an open bottom wall 132 that is contiguous with the fluid flow path 124. As shown, two of the slanted sidewalls 130 cooperate to form in part the receptacle 122, which is also formed in part by a slanted protrusion 108.

The open bottom wall 132 of the region of concavity 120 is sized to effectively block air bubbles and large particulates from entering the fluid flow path 124. It also allows surface pressure to stop initial fluid flow such that, in use, fluid will not enter the fluid flow path 124 through the open bottom wall 132 until a front of fluid from the receptacle 122 reaches the open bottom wall 132 while passing through the fluid flow path 124. This assists in both drawing in fluid from the region of concavity 120 while reducing the likelihood of bubbles entering the fluid flow path 124 or otherwise interrupting the fluid in the fluid flow path 124 with air.

Figure 11:
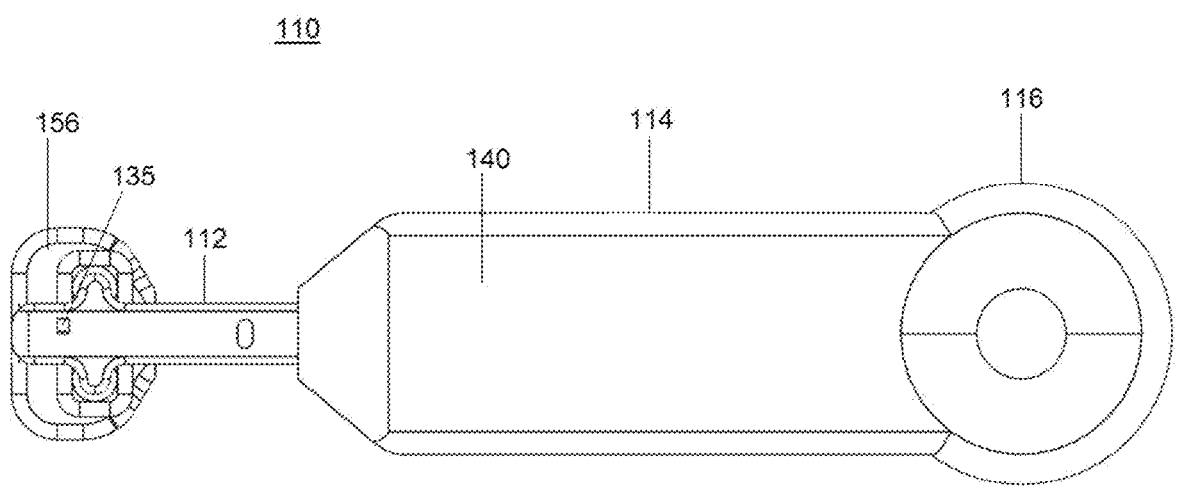
FIG. 11 shows a bottom plan view of the lateral flow device of FIG. 10.
Figure 12:
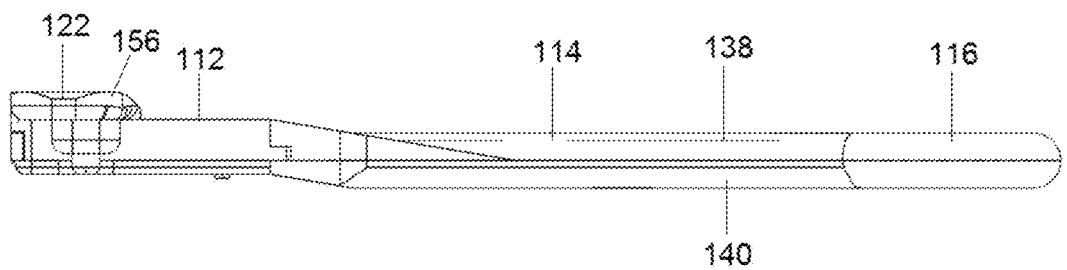
FIG. 12 shows a side view of the lateral flow device of FIG. 10.
Figure 13:
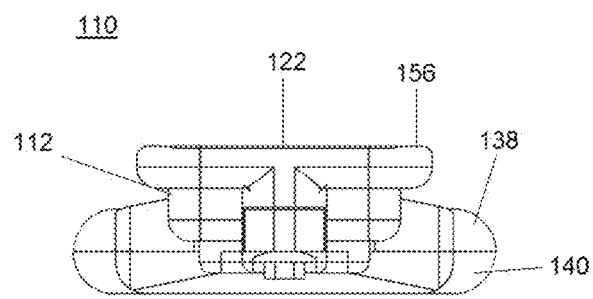
FIG. 13 shows a front view of the lateral flow device of FIG. 10.
Figure 14:
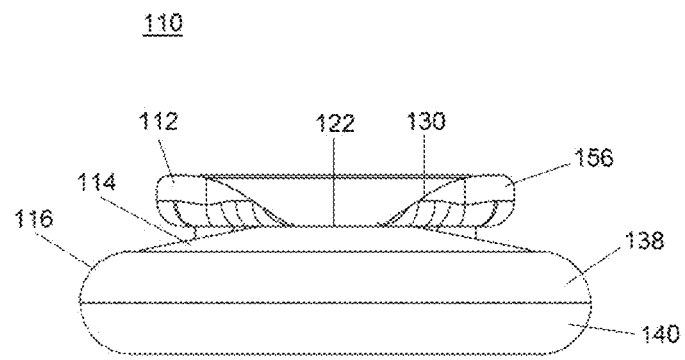
FIG. 14 shows a back view of the lateral flow device of FIG. 10.
Figure 15:
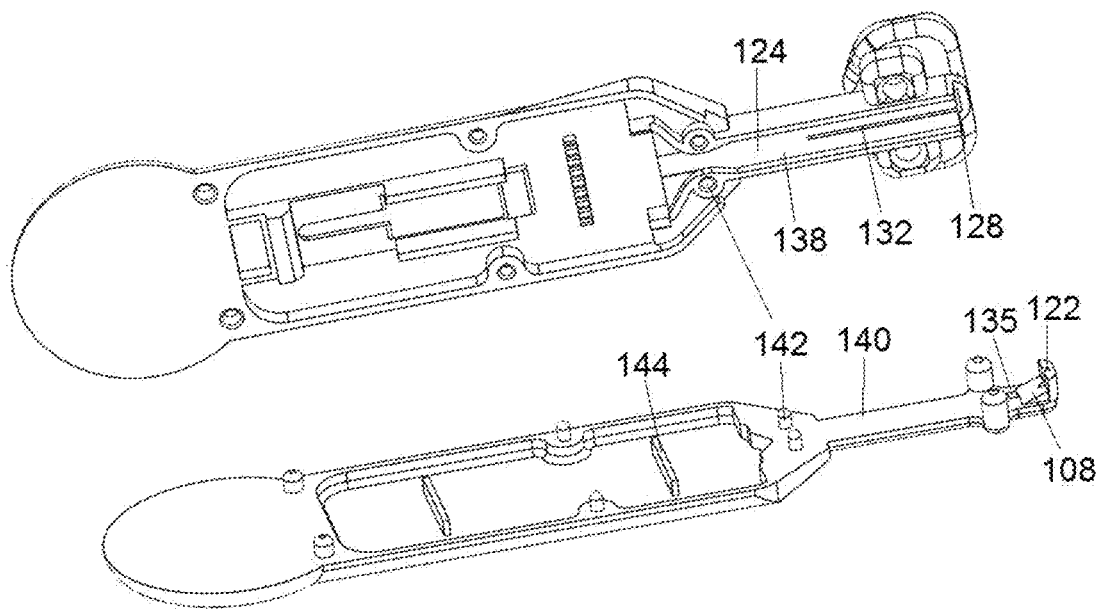
FIG. 15 shows a top and bottom exploded perspective view of the lateral flow device of FIG. 10.

As shown in FIGS. 11, 15, and 16, the fluid flow path 124 comprises a vent 135 near the receptacle 122 located in the bottom wall of the fluid flow path. Typically, the vent 135 opening is significantly wider than the openings of the receptacle 122 and the open bottom wall 132 allowing surface pressure to be reduced. For example, the vent 135 is typically about 1.5 to about 2.5 times wider than the openings of the receptacle 122 and/or the open bottom wall 132, such as about 1.5, about 1.6, about 1.7, about 1.8, about 1.9, about 2.0, about 2.1, about 2.2, about 2.3, about 2.4, or about 2.5 times wider. In a particular aspect, the vent 135 is typically about 0.8 to about 1.0 mm wide, whereas the openings of the receptacle 122 and/or the open bottom wall 132 are about 0.3 to about 0.5 mm wide.

If no fluid is present above the fluid flow path 124, once the fluid flow path 124 is totally or partially filled, fluid surfaces formed at the openings of the receptacle 122 and the open bottom wall 132 may stop fluid in the fluid flow path 124 from flowing downstream due to opposite surface pressure generated at the openings of the receptacle 122 and the open bottom wall 132 by surface tension. However, air may break into the fluid flow path 124 through the vent 135, thereby facilitating continued downstream fluid flow in the fluid flow path 124.

In other words, fluid normally enters the fluid flow path 124 until there is no more fluid above the fluid flow path 124, at either the receptacle 122 or the open bottom wall 132. At this moment the new surface formed at the openings of the receptacle 122 and the open bottom wall 132 will stop fluid flow in the fluid flow path 124 because the fluid flow path 124 is much wider than the openings of the receptacle 122 and the open bottom wall 132. Therefore the capillary force generated towards the downstream direction is less than the opposite capillary force generated by the surfaces at the openings of the receptacle 122 and the open bottom wall 132. The fluid also cannot overcome the capillary force at the vent 135 because the fluid flow path 124 and the vent 135 have a similar size. However, if the fluid has reached a lateral flow membrane 126, which has a stronger capillary force, the fluid will be able to overcome the capillary force at the vent 135 leading to continued fluid flow to the lateral flow membrane 126, even if it may still not be able to overcome the opposite capillary force at the openings of the receptacle 122 and the open bottom wall 132.

The collection unit 112 may be integral with the device 110 or it may be separable from the rest of the device 110. In certain aspects, the collection unit 112 is frangibly coupled into the device 110 so that the collection unit 112 can be easily snapped off after use for disposal and/or for inserting the rest of the device 110 into a reader for measuring the test result, as such readers may not be sized to fit the collection unit 112 when attached to the body 114.

The collection unit 112 is typically provided with a cover 136 as shown in FIG. 16. The cover 136 is removable so that the collection unit 112 can be used. The cover 136 can then be placed back on the collection unit 112 for sanitary and/or protective reasons. The cover 136 may be completely removable or it may, in aspects, remain partially attached to the device 110 and/or the collection unit 112 to reduce the chances of the cover 136 being misplaced or otherwise contaminated.

The device 110 typically comprises a handle 116, which, like the collection unit 112 may be frangibly coupled in the device 110 so that the handle 116 can be snapped away from the rest of device 110 and a conventional reader can be used with the rest of device 110. The handle 116 is typically rounded with an indent sized to facilitate handling with a thumb or finger.

The device 110 is typically formed by mated upper 138 and lower 140 portions, as shown in FIGS. 15 and 16, for ease of manufacturing and insertion of a desired lateral flow membrane 126. The device 110 could also be formed as a single unit. As shown, there are mated friction-fit components 142 that hold the upper 138 and lower 140 portions together. The upper 138 and lower 140 portions also contain guides 144 that securely hold the lateral flow membrane 126 in position so that it is in fluid communication with the fluid flow path 124.

As can be seen in FIGS. 15 and 16, the region of concavity 120 and fluid flow path 124 are formed in the upper portion 138 of the device 110. The receptacle 122 is formed in the lower portion 140 of the device 110. It will be understood that one or more of these features could be formed in part or in whole by the either portion 138, 140 of the device 110.

FIGS. 17-24 show a third lateral flow device 210, which is similar to the second lateral flow device 110, but produced in several pieces so that part of the device 210 is removable to be able to fit into a conventional reader device. As shown, the device 210 comprises a holder 202, a reader body 204 comprised of an upper portion 238 and a lower portion 240, and a cover 236 for the reader body 204. When assembled, the device 210 comprises a fluid collection unit 212 and a body 214, much like the devices 10, 110 described above. The body 214 contains a handle 216 and a cavity to hold the reader body 204, which has a window 218, through which results of an assay can be read visually or by machine. The device 210 is typically transparent, but can be of any desired color and opacity and combinations thereof, provided the test can still be read. It will be understood that in a completely transparent device 210, the window 218 is optional.

As above, the fluid collection unit 212 typically comprises an elongate body comprising a region of concavity 220 and a receptacle 222. Receptacle 222 is simply a small channel or opening leading to a fluid flow path 224. The region of concavity 220 also leads to the fluid flow path 224, as described above. The fluid flow path 224 functions to direct a fluid sample from the receptacle 222 to a lateral flow membrane 226 at opposite ends of the collection unit 212. As shown in FIGS. 17-20, the receptacle 222 is surrounded by flanges 256 that assist in collecting and directing the fluid sample towards the receptacle 222.

Figure 17:
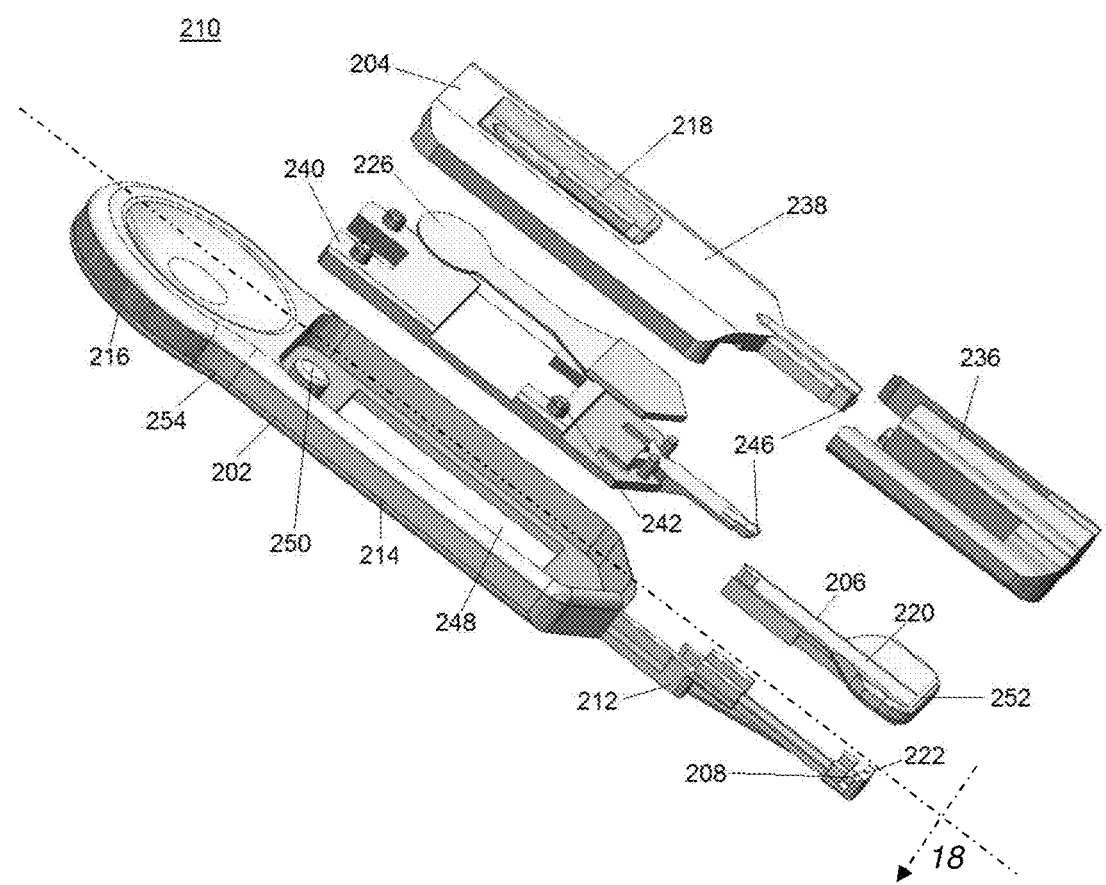
FIG. 17 shows a top exploded perspective view of a third embodiment of a lateral flow device described herein.
Figure 18:
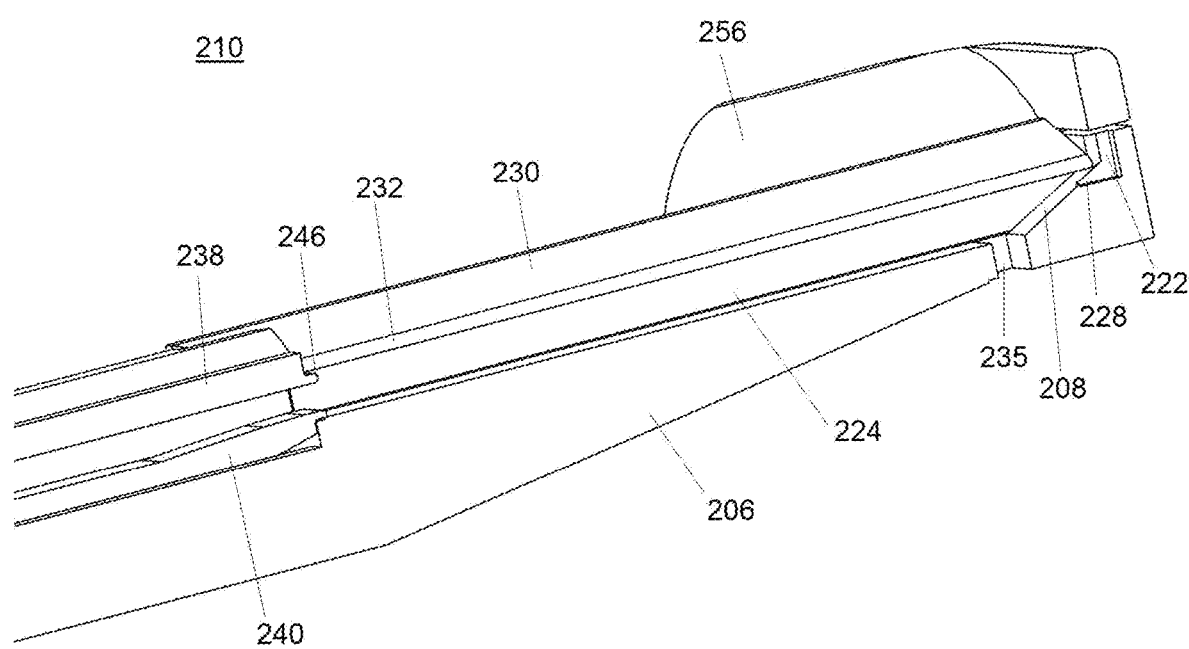
FIG. 18 shows a cross-sectional view of the fluid collection unit along line 18-18 of the lateral flow device of FIG. 17.
Figure 19:
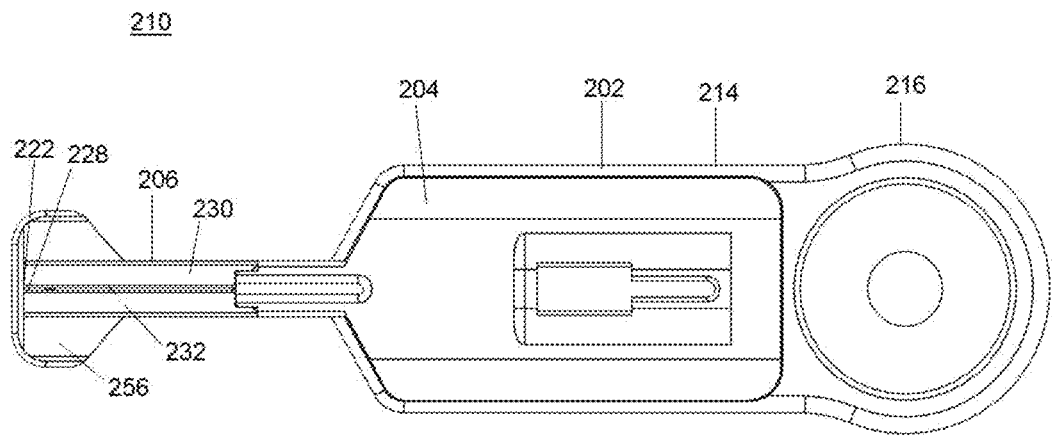
FIG. 19 shows a top plan view of the lateral flow device of FIG. 17 in the absence of a device cover.

As can be seen in FIGS. 17 and 18, the fluid flow path 224 is formed by mating a fluid collection portion 206 with the proximal end of the holder 202 and by mating a top portion 238 and a bottom portion 240 of the reader body 204. The top portion 238 and bottom portion 240 of the reader body 204 comprise protrusions 246 that overlap with the surface of the fluid flow path 224. This overlapping prevents a gap from forming between the proximal end of the fluid flow path 224, formed by mating the fluid collection portion 206 with the proximal end of the holder 202, and the distal end of the fluid flow path, formed by mating the top portion 238 and bottom portion 240 of the reader body 204.

In certain aspects, the volume held by the fluid flow path 224 is rationally selected so as to be equal to or greater than the volume required for accurate function of the lateral flow membrane 226. In this way, the test will not initiate until a sufficient amount of sample is present in the collection unit 212, as the fluid front must reach the lateral flow membrane 226 for the test to begin. In aspects, the fluid flow path 224 has a volume of from about 10 µl to about 200 µl, such as from about 10 µl to about 100 µl, such as from about 25 µl to about 50 µl, such as about 40 µl.

The receptacle 222 is typically a small vertical channel integrally formed in the collection unit 212. The receptacle 222 has an open sidewall 228 through which fluid in the receptacle 222 can enter the fluid flow path 224. The region of concavity 220 assists in directing additional fluid towards the receptacle 222.

As shown, the region of concavity 220 is formed in a wall above the fluid flow path 224 and comprises three slanted walls 230 that converge together at an open bottom wall 232 that is contiguous with the fluid flow path 224. As shown, two of the slanted sidewalls 230 cooperate to form in part the receptacle 222, which is also formed in part by a slanted protrusion 208.

The open bottom wall 232 of the region of concavity 220 is sized to allow surface pressure to stop fluid flow such that, in use, fluid will not enter the fluid flow path 224 through the open bottom wall 232 until a front of fluid from the receptacle 222 reaches the open bottom wall 232 while passing through the fluid flow path 224. This assists in both drawing in fluid from the region of concavity 220 while reducing the likelihood of bubbles entering the fluid flow path 224 or otherwise interrupting the fluid in the fluid flow path 224 with air.

Figure 20:
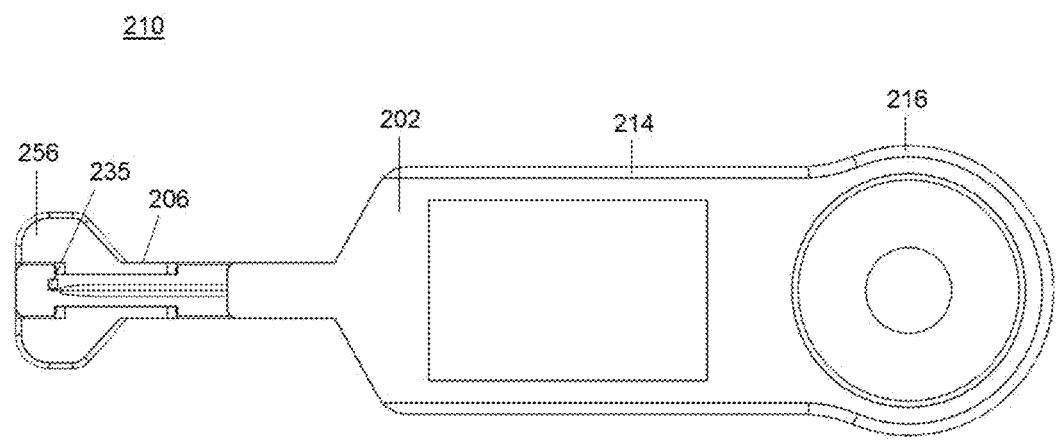
FIG. 20 shows a bottom plan view of the lateral flow device of FIG. 17 in the absence of a device cover.
Figure 21:
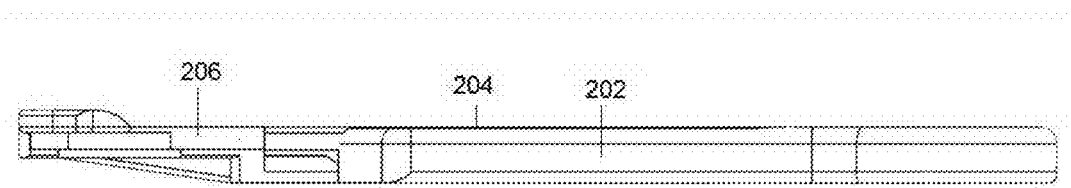
FIG. 21 shows a side view of the lateral flow device of FIG. 17 in the absence of a device cover.
Figure 22:
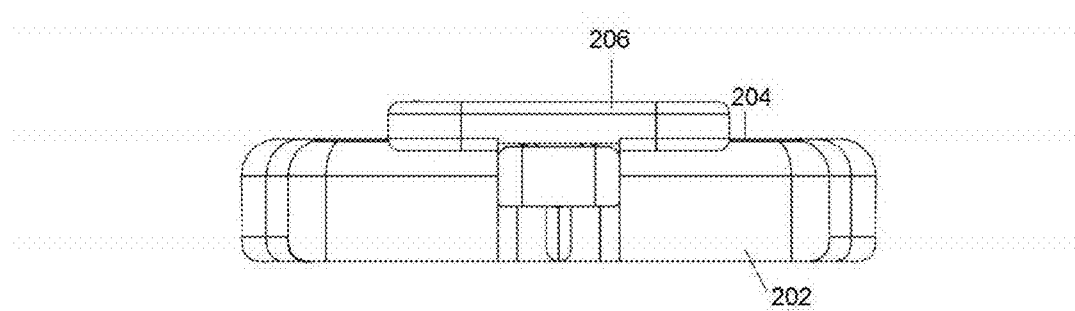
FIG. 22 shows a front view of the lateral flow device of FIG. 17 in the absence of a device cover.
Figure 23:
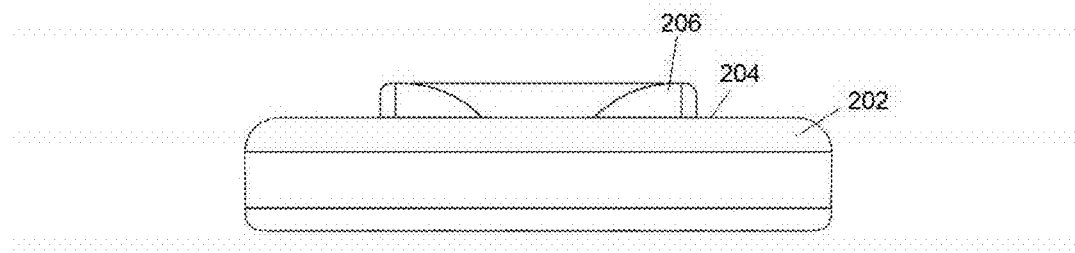
FIG. 23 shows a back view of the lateral flow device of FIG. 17.

As shown in FIGS. 18 and 20, the fluid flow path 224 comprises a vent 235 near the receptacle 222 located in the bottom wall of the fluid flow path. Typically, the vent 235 opening is significantly wider than the openings of the receptacle 222 and the open bottom wall 232 allowing surface pressure to be reduced. If no fluid is present above the fluid flow path 224, once the fluid flow path 224 is totally or partially filled, fluid surfaces formed at the openings of the receptacle 222 and the open bottom wall 232 may stop fluid in the fluid flow path 224 from flowing downstream due to opposite surface pressure generated at the openings of the receptacle 222 and the open bottom wall 232 by surface tension. However, air may break into the fluid flow path 224 through the vent 235, thereby facilitating continued downstream fluid flow in the fluid flow path 224. In other words, fluid normally enters the fluid flow path 224 until there is no more fluid above the fluid flow path 224, at either the receptacle 222 or the open bottom wall 232. At this moment the new surface formed at the openings of the receptacle 222 and the open bottom wall 232 will stop fluid flow in the fluid flow path 224 because the fluid flow path 224 is much wider than the openings of the receptacle 222 and the open bottom wall 232. Therefore the capillary force generated towards the downstream direction is less than the opposite capillary force generated by the surfaces at the openings of the receptacle 222 and the open bottom wall 232. The fluid also cannot overcome the capillary force at the vent 235 because the fluid flow path 224 and the vent 235 have a similar size. However, if the fluid has reached a lateral flow membrane 226, which has a stronger capillary force, the fluid will be able to overcome the capillary force at the vent 235 leading to continued fluid flow to the lateral flow membrane 226, even if it may still not be able to overcome the opposite capillary force at the openings of the receptacle 222 and the open bottom wall 232. If the fluid has not reached the lateral flow membrane 226 and no more sample is left above the fluid flow path 224, the flow will stop until more sample is added. In this way, the configuration of the device ensures that the test is only initiated when there is enough sample in the device.

In this aspect, the reader body 204 is shaped and sized to fit a conventional reader device and is removable from the holder 202 for insertion into the reader device. Once the test is complete, the reader body 204 is removed from the device 210, an optional cover 236 is placed over the reader body 204 to prevent contamination of the reader device, and the reader body 204 is inserted into the reader for measuring the test result. The reader body 204 together with cover 236 is shown separate from the device 210 in FIG. 24.

Thus, it will be understood that the reader body 204 may be disposable, whereas the holder 202 may be reusable and optionally sterilisable. In this way, a single patient requiring repeated testing may reuse the holder multiple times or the holder may be sterilized for use between different patients in a clinic or hospital setting. The holder 202, reader body 204, and cover 236 may be made from the same or different materials and may independently be transparent, translucent, or opaque, or a combination thereof.

As shown in FIGS. 17 and 20, the holder 202 comprises an open region 248 that facilitates removal of the reader body 204 from the holder 202. For example, a user can push through the open region 248 in order to expel the reader body 204 from the holder 202. In aspects, the holder 202 also includes a protrusion 250 that assists in properly aligning the reader body 204 in the holder 202 and optionally offers a friction fit mating that assists in keeping the reader body 204 tightly in the holder 202 until it is desired to be removed by force.

Figure 24:
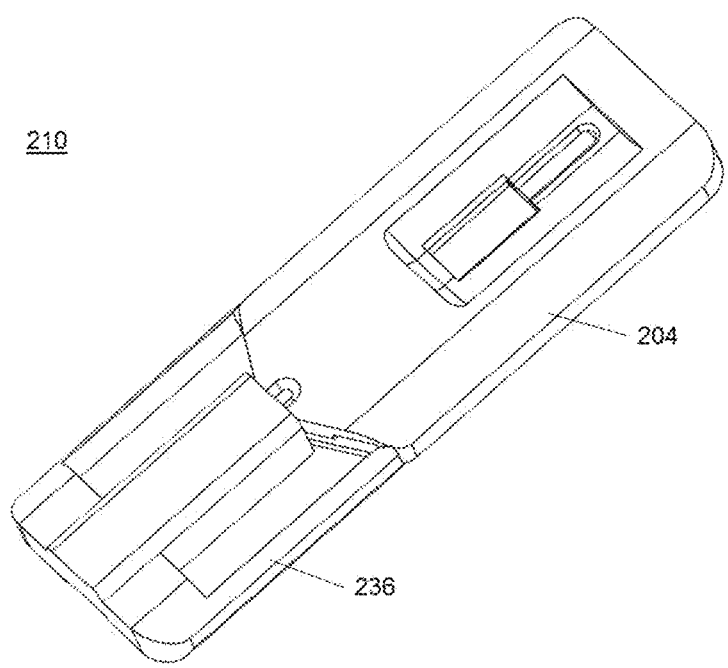
FIG. 24 shows a perspective view of a reader body portion of the lateral flow device of FIG. 17.

As noted above, the reader body 204 is typically provided with a cover 236 as shown in FIGS. 17 and 24. The cover 236 is removable so that the reader body 204 can be inserted into the holder 202 and used. The cover 236 can then be placed back on the reader body 204 when it is removed from the holder 202 for sanitary and/or protective reasons and/or for proper fit in a reader device. The cover 236 may be completely removable or it may, in aspects, remain partially attached to the device 210 and/or the reader body 204 to reduce the chances of the cover 236 being misplaced or otherwise contaminated.

The holder 202 typically comprises a handle 216, which is typically rounded with an indent sized to facilitate handling with a thumb or finger.

The reader body 204 is typically formed by mated upper 238 and lower 240 portions, as shown in FIGS. 17 and 24, for ease of manufacturing and insertion of a desired lateral flow membrane 226. The reader body 204 could also be formed as a single unit. As shown, there are mated friction-fit components 242 that hold the upper 238 and lower 240 portions together. The upper 238 and lower 240 portions also contain guides (not shown) that securely hold the lateral flow membrane 226 in position so that it is in fluid communication with the fluid flow path 224.

The holder 202 is similarly formed from mated upper 252 and lower 254 portions, as shown in FIGS. 17 and 18. The lower portion 254 contains the handle 216, the body 214, and the bottom half of the proximal end of the fluid flow path 224. The upper portion 252 is much smaller than the top portion 254 and contains the region of concavity 220 and open bottom wall 232. These upper 252 and lower 254 portions mate together with friction to form the proximal end of the fluid flow path 224.

As can be seen in FIGS. 17 and 18, the region of concavity 220 and fluid flow path 224 are formed in the upper portion 252 of the holder 202. The receptacle 222 is formed in the lower portion 254 of the holder 202. It will be understood that one or more of these features could be formed in part or in whole by the either portion 252, 254 of the holder 202.

It will be understood that any lateral flow membrane could be used in the devices described herein and/or in conjunction with the collection units described herein. In a particular aspect, the lateral flow membrane is as described in U.S. Pat. Nos. 7,785,865, 8,119,393, or 7,238,538 or in International Patent Application Publication Nos. WO 2009/143601 or WO 2013/155617.

While the collection units described herein are particularly suited for use in collecting a saliva sample, it will be understood that they may find use in collecting any fluid, such as, for example, serum, blood, plasma, a cell suspension, cell culture supernatant, saliva, oral fluid, cerebrospinal fluid, amniotic fluid, milk, colostrum, mammary gland secretion, lymph, urine, sweat, lacrimal fluid, gastric fluid, synovial fluid, mucus, or combinations thereof.

Further, the collection units described herein have been described for use in combination with a lateral flow assay in which generally small volumes of sample is needed. However, it will be understood that these collections units may be used to collect saliva for any purpose and may be appropriately sized in order to collect any desired volume of saliva, which may vary depending upon the desired end use. For example, if the saliva is being collected for a DNA sequencing end use, then up to about 5 ml of saliva may be collected, such as from about 0.5 ml to about 5 ml, such as from about 1 ml to about 3 ml, such as about 2 ml.

As noted above, the constriction 34 is typically formed by reducing the cross-sectional area of the fluid flow path 24, such as by increasing the thickness of the top wall of the fluid flow path 24. It will be understood that the constriction 34 could be formed by increasing the thickness of the top and/or bottom walls of the fluid flow path and the constriction 34 could be of any desired shape, such as a gradual or abrupt narrowing of the flow path in the upstream or downstream direction.

Methods of Use

In use, a fluid collection unit 12, 112, 212 described herein is placed near or in a fluid sample. When the fluid sample is saliva, the fluid collection unit 12, 112, 212 is placed in the mouth such as under the tongue or in the cheek area. The collection unit 12, 112, 212 then passively collects saliva as it is produced in the mouth, without the need for expectorating or otherwise swabbing the mouth.

As fluid collects in the receptacle 22, 122, 222, it is drawn into the fluid flow path 24, 124, 224 by capillary action. The constriction 34, when present, increases capillary force opposite to the fluid flow direction when sufficient liquid is not available and thereby reduces the likelihood of a bubble entering the fluid flow path 24, 124, 224. As the front of saliva flows along the fluid flow path 24, 124, 224, it will collect fluid that has entered the region of concavity 20, 120, 220 due to the destruction of fluid surface tension at the open bottom wall 32, 132, 232, which had theretofore prevented fluid in the region of concavity 20, 120, 220 from entering the fluid flow path 24, 124, 224.

The size of the open bottom wall 32, 132, 232 at the bottom of the region of concavity 20, 120, 220 is designed so that the surface pressure is sufficient to stop fluid flow into the fluid flow path 24, 124, 224 via the open bottom wall 32, 132, 232 unless the fluid flow path 24, 124, 224 is filled with fluid or until a front of fluid in the fluid flow path 24, 124, 224 contacts fluid at the open bottom wall 32, 132, 232, thereby drawing the fluid into the fluid flow path 24, 124, 224. This not only reduces the risk that the receptacle may be blocked by solid materials existed in fluid sample such as cells and bacteria but also reduces chances for bubbles to enter the fluid flow path 24, 124, 224. Thus, as the front of fluid is drawn along the fluid flow path 24, 124, 224 by capillary action, the liquid surface at the open bottom wall 32, 132, 232 is removed so that fluid held at the open bottom wall 32, 132, 232 by surface pressure can be drawn into fluid flow path. This increases the efficiency of the collection unit 12, 112, 212, as it is able to collect fluid from the region of concavity 20, 120, 220 in addition to fluid present in the receptacle 22, 122, 222.

When the fluid reaches the end of the fluid flow path 24, 124, 224, it may enter a lateral flow membrane 26, 126, 226, where an assay will be carried out and a test result can be observed. The fluid may alternatively be used in other ways, or it may be collected and stored for future use.

The above disclosure generally describes the present invention. Changes in form and substitution of equivalents are contemplated as circumstances may suggest or render expedient. Although specific terms have been employed herein, such terms are intended in a descriptive sense and not for purposes of limitation.

All publications, patents, and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

That which is claimed is:

1. A fluid collection unit comprising:
a receptacle for passively collecting a fluid sample; and
a fluid flow path comprising a vent and in fluid communication with the receptacle, the vent comprising an opening that is about 1.5 to about 2.5 times wider than an opening of the receptacle, the fluid flow path passing through the unit for directing the fluid sample from the receptacle at a proximal end of the unit to an opposing, distal end of the unit;
wherein the receptacle comprises a vertical channel comprising an open sidewall in fluid communication with the fluid flow path, and a region of concavity for directing fluid towards the receptacle, wherein the region of concavity is formed in a wall of the unit and is substantially parallel with and above the fluid flow path,
wherein the region of concavity comprises an open bottom wall in fluid communication with the fluid flow path,
wherein the open bottom wall is sized so that large air bubbles or solid materials can be blocked from entering the fluid flow path,
wherein the unit allows for collection and flow of the fluid from an opening in the receptacle through the open sidewall and into the proximal end of the unit and to the distal end of the unit and into a lateral flow membrane in fluid communication with the unit in a single step, and wherein the fluid is oral fluid.

2. The collection unit of claim 1, wherein the vent is in the bottom wall of the fluid flow path.

3. The collection unit of claim 1, wherein the vent is at the proximal end of the fluid flow path.

4. The collection unit of claim 1, wherein the receptacle comprises an indentation in the fluid collection unit.

5. The collection unit of claim 4, wherein the indentation is substantially cylindrical and comprises an open sidewall in fluid communication with the fluid flow path.

6. The collection unit of claim 1, wherein the receptacle is formed within a slanted protrusion.

7. The collection unit of claim 1, wherein the receptacle is surrounded by flanges to direct the fluid sample to the receptacle.

8. The collection unit of claim 1, wherein the open bottom wall is sized to allow sufficient surface pressure such that, in use, fluid will not enter the fluid flow path through the open bottom wall until a front of fluid reaches the open bottom wall while passing through the fluid flow path.

9. The collection unit of claim 1, wherein the fluid flow path comprises a proximal constriction.

10. The collection unit of claim 1, wherein the fluid flow path holds from about 10 µl to about 200 µl of fluid.

11. The collection unit of claim 1, wherein the fluid flow path is in communication with the lateral flow membrane.

12. The collection unit of claim 1, further comprising a cover.

13. The collection unit of claim 1, wherein the collection unit does not comprise an absorbent pad or sponge for collecting the fluid and/or wherein the collection unit does not require the addition of a buffer or diluent to effect flow of the fluid through the fluid flow path.

14. A lateral flow device comprising the fluid collection unit of claim 1.

15. The device of claim 14, wherein the fluid collection unit is detachable from the lateral flow device.

16. The device of claim 14, wherein the lateral flow device is transparent.

17. The device of claim 14, wherein the lateral flow device comprises a handle and wherein the handle is an indented circle for supporting a thumb or finger.

18. The device of claim 17, wherein the handle is detachable from the lateral flow device.

19. A reader body configured to engage with the fluid collection unit of claim 1, comprising a fluid flow path in fluid communication with the fluid flow path of the fluid collection unit, such that the fluid sample is capable of flowing from the proximal end of the fluid collection unit through to the distal end of the fluid collection unit and into the reader body.

20. The reader body of claim 19, comprising at least one protrusion for overlapping with the fluid flow path of the fluid collection unit.

21. A one-step method of collecting a substantially bubble-free sample, the method comprising inserting the collection unit of claim 1, in or near a sample and allowing the sample to be drawn into the fluid flow path.

22. The method of claim 21, wherein the sample is saliva and the method comprises inserting the collection unit into the mouth, such as under the tongue or in the cheek pocket.

23. A fluid collection unit comprising:
a receptacle comprising an opening for collecting a fluid sample;
a fluid flow path in fluid communication with the receptacle, the fluid flow path passing through the unit for directing the fluid sample from the receptacle at a proximal end of the unit to an opposing, distal end of the unit; wherein the receptacle comprises a vertical channel comprising an open sidewall in fluid communication with the fluid flow path; and
a vent in a bottom wall of the fluid flow path,
wherein the vent comprises an opening that is about 1.5 to about 2.5 times wider than the opening of the receptacle,
wherein the unit allows for collection and flow of the fluid from the receptacle through the open sidewall and into the proximal end of the unit and to the distal end of the unit and into a lateral flow membrane in fluid communication with the unit in a single step, and
wherein the fluid is oral fluid.

* * * * *